US006987591B2

(12) United States Patent
Shaker et al.

(10) Patent No.: US 6,987,591 B2
(45) Date of Patent: Jan. 17, 2006

(54) VOLUME HOLOGRAM (75) Inventors: Jafar Shaker, Richmond Hill (CA); Michel Cuhaci, Ottawa (CA); Apisak Ittipiboon, Kanata (CA)

(73) Assignee: Her Majesty the Queen in right of Canada, as represented by the Minister of Industry through the Communications Research Centre Canada, Ottawa (CA)

( * ) Notice: Subject to any disclaimer, the term of this patent is extended or adjusted under 35 U.S.C. 154(b) by 9 days.

(21) Appl. No.: 10/892,116

(22) Filed: Jul. 16, 2004

(65) Prior Publication Data

US 2005/0012972 A1    Jan. 20, 2005

Related U.S. Application Data

(60) Provisional application No. 60/487,612, filed on Jul. 17, 2003.

(51) Int. Cl.
*G02B 5/32* (2006.01)
(52) U.S. Cl. .......................... 359/15; 359/22; 359/24; 359/1; 385/31
(58) Field of Classification Search ................ 359/1, 359/11, 15, 19, 22, 24, 34, 566, 576; 343/912; 385/31, 37
See application file for complete search history.

(56) References Cited

U.S. PATENT DOCUMENTS

| 3,886,558 | A | 5/1975 | Cary et al. |
|---|---|---|---|
| 5,385,623 | A | 1/1995 | Diaz |
| 5,581,639 | A | 12/1996 | Davies et al. |
| 5,662,982 | A | 9/1997 | Diaz |
| 5,670,965 | A | 9/1997 | Tuovinen et al. |
| 5,990,850 | A * | 11/1999 | Brown et al. ............... 343/912 |
| 6,081,239 | A | 6/2000 | Sabet et al. |
| 6,097,271 | A | 8/2000 | Kozakoff |
| 6,646,605 | B2 | 11/2003 | McKinzie et al. |
| 6,660,193 | B2 | 12/2003 | Myhre |
| 2003/0002045 | A1 * | 1/2003 | Nemat-Nasser et al. .... 356/445 |
| 2003/0232179 | A1 * | 12/2003 | Steenblik et al. ......... 428/195.1 |
| 2004/0258353 | A1 * | 12/2004 | Gluckstad et al. ............ 385/28 |

OTHER PUBLICATIONS

"Millimeter Wave Beam Shaping using Holograms", Meltaus et al, IEEE Transactions on Microwave Theory and Techniques, vol. 51, No. 4, Apr. 2003.

"Introduction to Fourier Optics", Goodman J.W., McGraw-Hill, New York, 1996.

"The Relative Permittivity of Tetragonal Arrays of Perfectly Conducting Thin Discs", Brown et al, Proc. IEEE, paper 1702R, Jan. 1995.

(Continued)

*Primary Examiner*—Fayez G. Assaf
(74) *Attorney, Agent, or Firm*—Neil Teitelbaum; Doug MacLean; Teitelbaum & MacLean (57) ABSTRACT

A volume hologram for modifying a characteristic of an input microwave beam and a method for manufacturing thereof are disclosed. The hologram is fabricated from a multi-layer artificial dielectric wherein each layer is made of a dielectric material and includes a lattice of inclusions, for example metal disks disposed on one side thereof, and wherein a pre-determined three-dimensional grating pattern of dielectric perturbations is induced by spatial modulating the lattice of the inclusions. The hologram can be designed for efficiently steering, reshaping, combining or splitting microwave beams.

19 Claims, 6 Drawing Sheets

OTHER PUBLICATIONS

"Analysis of Optical Propagation in Thick Holographic Gratings", Alferness R, Applied Physics, vol. 7, 1995, pp 29-33.

"Coupling in Doubly Exposed Holographic Grating", Alferness R., J. Optic. Soc. Am., vol. 65(6), 1974, pp. 730-739.

"Artificial Dielectric Lens Antennas: Assessment of the Potential for Space Applications", Abella et al, Sep. 1993.

"Computer Generated Holograms for MM- and SUBMM-Wave Applications" Raisanen et al, CATR, Bessel Beams and Radiowave Vortices 9th International Conf. Of Terahertz Electronics Oct. 15-16, 2001 (invited paper).

* cited by examiner

VOLUME HOLOGRAM

CROSS-REFERENCE TO RELATED APPLICATIONS

This application claims priority of U.S. Provisional Application No. 60/487,612 filed Jul. 17, 2003, entitled "Thick Volume Hologram for Microwave Frequency Band and Estimation of Unreliable Digital Speech Samples via Composite Modelling and Adaptive Filtering", which is incorporated herein by reference for all purposes.

FIELD OF THE INVENTION

The present invention generally relates to holographic elements for modifying electromagnetic beams, and in particular relates to volume multilayer artificial dielectric holograms for modifying microwave beams.

BACKGROUND OF THE INVENTION

Holographic elements have been extensively used in the optical frequency band for a variety of applications such as beam switching, beam shaping, data storage, etc. In a traditional holographic scheme, an interference of two beams, which are usually referred to as a reference beam and an object beam, in a photosensitive film is used to fabricate a hologram for applications in the optical frequency band. The interference pattern of the two beams can be imprinted in the photosensitive volume of the film by a post-processing, resulting in a modulation of the refractive index in a transverse plane, or in other words to an appearance of a grating-like pattern of dielectric perturbations in the film. A holographic element fabricated thereby, when illuminated by the reference beam, will reproduce the object beam due to diffraction of the former on the grating pattern. In some applications such as beam switching or beam shaping the reference beam can therefore be referred to also as an input beam, and the object beam—as an output beam.

Holograms are often divided into two categories, depending on a thickness of the grating structure and on a beam conversion efficiency defined as a ratio of the output beam power to the input beam power: thin holograms, having an essentially two-dimensional (2D) pattern of dielectric perturbations typically thinner than a wavelength of the input beam, and thick or volume holograms, which typically have thickness on the order of the wavelength or more. Generally, only a portion of the input beam power is converted to the output beam power by a hologram, with the rest being either lost due to material attenuation and spurious reflections, or transferred into a set of detrimental side beams formed by waves diffracted into lower- and/or higher-order diffraction directions. Thin holograms wherein every part of the input beam radiation within its aperture experiences a substantially single diffraction event while propagating through the film, have a limited conversion efficiency, generally not exceeding 36%, and most of the beam power is lost to the side beams propagating in other diffraction orders. Conversely, in thick volume holograms multiple consecutive diffraction events on the dielectric perturbations can theoretically increase the conversion efficiency to up to 100%, so that most of the input beam power can be transferred into the output beam. Therefore thick volume holograms have a considerable advantage over thin holograms as being potentially much more efficient in beam modifying applications.

In a microwave frequency band, sometimes also referred to as a radio-frequency band and understood herein as including the cm, mm and sub-mm wavelength range corresponding to a frequency range 10–1000 GHz, holographic elements for such applications as beam steering or beam shaping have been exploited to a much lesser degree than in optics, mostly due to difficulties of transferring the well-developed optical technologies for hologram fabrication into the microwave region.

First, traditional methods of holographic fabrication by imprinting the interference pattern of two beams in a photographic material is not easily transferable into the microwave frequency band due to a lack of efficient photo-imprinting technologies for wavelengths much higher than optical. This difficulty has been overcome in computer-generated holograms, wherein a binary or m-ary grating pattern for converting an input beam into an output beam is generated by a computer after appropriate diffraction simulations, and then transferred into either an appropriate surface profile of a dielectric film or plate for phase holograms, or into a pattern of opaque obstacles with a spatial period about or exceeding half of the beam wavelength for amplitude holograms.

Computer-generated holograms of this type for shaping and re-directing microwave beams in the mm and cm wavelength bands were described for example by J. Meltaus et al. in an article "Millimeter wave beam shaping using holograms", IEEE Transactions on Microwave Theory and techniques, vol. 51, No.4, April 2003. U.S. Pat. No. 5,670, 965 to Tuovinen et al. discloses a compact antenna test range for performing antenna and radar cross-section measurements having a transmitter for transmitting an electromagnetic wavefront and at least one radio frequency hologram of the aforedescribed type for receiving the wavefront, converting the wavefront into a plane wave, and passing on the plane wave at an oblique angle with respect to a central axis of the hologram for illuminating a piece to be tested.

However, to the best of the inventors' knowledge, no thick volume hologram for the microwave frequency band wherein the detrimental side beams are suppressed has been disclosed so far. Furthermore, heretofore low loss efficient holograms having a desirable thick three-dimensional pattern of dielectric perturbations for the microwave frequency band have been difficult to manufacture.

On the other hand, a 3D profiling of the dielectric constant at microwave frequencies can be achieved in such materials as artificial dielectrics. An artificial dielectric can be viewed as a large-scale model of an actual dielectric, obtained by arranging in a host dielectric material a large number of identical conducting or non-conducting inclusions in a regular or irregular three-dimensional lattice so that spacing between centers of the inclusions is much smaller than a wavelength of microwave field therein. Depending on the spacing of the inclusions from each other and on their size, a range of values can be realised for a dielectric permittivity of the structure, which is different from the dielectric permittivity of the host material. Similar to natural dielectrics which owe their higher than unity refractive index to an electrical polarisation of its constituent molecules in an external electric field, the inclusions in artificial dielectrics give rise to the same effect if their size and spacing are much smaller than the wavelength $\lambda$ of the exerted time varying electric field, typically about or less than $\lambda/10$.

The ability of a dielectric material to be electrically polarized by an external electromagnetic field is commonly expressed in terms of relative permittivity, commonly defined as a ratio of permittivity of the material to permittivity of free space. The relative permittivity is also referred to as a dielectric constant. For purposes of this application, permittivity means relative permittivity or the dielectric constant unless otherwise indicated.

Artificial dielectrics have been used for fabrication of microwave lenses, either by appropriate shaping of the input/output surfaces of a block of an artificial dielectric as commonly done in conventional lenses, or by creating a non-homogenous medium wherein a 3D shaping of the effective dielectric constant, or the effective permittivity, is obtained by appropriately varying the size and/or spacing between the inclusions to achieve a focusing effect in a flat block of artificial dielectric.

A known method of fabricating an artificial dielectric, wherein a 3D shaping of the effective dielectric constant can be conveniently obtained, uses periodic patterns of metallic patches printed upon stacked dielectric layers. If a separation between layers and a size of metallic print is less than about a tenth of a wavelength of an incident electromagnetic wave, dielectric properties of the structure at the wavelength of the incoming wave can be characterized by an equivalent dielectric constant whose value can be changed by varying geometrical parameters of the structure such as an inter-layer spacing, size and separation of the metallic patches.

The aforedescribed layered artificial dielectric materials have been used for the manufacturing of flat inhomogeneous microwave lenses, wherein the effective dielectric constant is gradually changed on a scale of several wavelengths by a gradual variation of the inclusions' size or spatial density, so to produce a focusing effect for an incident microwave beam by means of refraction.

An object of this invention is to provide a volume hologram having a 3D lattice of inclusions arranged to form a volume dielectric grating for modifying an electromagnetic beam by diffraction thereupon.

Another object of this invention is to provide a volume hologram fabricated in an artificial dielectric comprising a plurality of dielectric sheets with 2D lattices of inclusions arranged to form a staked plurality of modulated dielectric layers for modifying a microwave beam.

Another object of this invention is to provide a method of fabrication of volume holograms for applications in the microwave frequency band using artificial dielectric technology.

SUMMARY OF THE INVENTION

In accordance with the invention, a volume hologram for modifying an input electromagnetic beam having a wavelength $\lambda$ and propagating in an input direction is provided comprising a host material having a dielectric constant and a beam receiving region for receiving the input electromagnetic beam, a 3D lattice of isolated inclusions incorporated in the beam receiving region of the host material, each said inclusion having a size and a center, wherein said inclusions are disposed with a characteristic spacing between centers thereof about or smaller than one tenth of the wavelength for providing the volume hologram with an effective dielectric constant $\epsilon$ different from a dielectric constant of the host material, and wherein said 3D lattice of inclusions is modulated for inducing a pre-determined 3D pattern of dielectric perturbations in the beam receiving region of the host material, said pre-determined 3D pattern of dielectric perturbations having multiple regions of increasing dielectric constant alternating with regions of decreasing dielectric constant in a direction normal to the input direction, for modifying the input electromagnetic beam by diffraction thereupon.

In accordance with a further aspect of this invention, the host material of the volume hologram comprises a plurality of $M \geq 10$ dielectric sheets disposed sequentially in a first direction and forming a stacked layered structure crossing the input direction, wherein each of the N dielectric sheets incorporates a 2D modulated lattice of the inclusions with a lattice period about or less than 0.1 $\lambda$ arranged for inducing a 2D pattern of dielectric perturbations, and wherein the M 2D patterns of dielectric perturbations thereby provided form the pre-determined 3D pattern of dielectric perturbations.

In accordance with a further aspect of the invention, the volume hologram is for modifying at least one of a direction or a shape of a microwave beam having the wavelength corresponding to frequency range between 10 GHz and 1000 GHz.

In accordance with another aspect of the invention, a method of fabrication of a volume microwave hologram for modifying a microwave beam is provided, said method comprising steps of (a) identifying parameters of input and output microwave beams, said parameters including a wavelength, an input direction and an output direction of the microwave beam, an input wave front shape and an output wave front shape of the microwave beam; (b) identifying a plurality of 2D patterns of dielectric perturbations and a spatial separation between said 2D patterns for forming a 3D pattern of dielectric perturbations from the plurality of stacked 2D patterns of dielectric perturbations for changing at least the direction of the microwave beam from the input direction to the output direction by diffraction on the 3D pattern of dielectric perturbations, said 2D patterns of dielectric perturbations including multiple regions of increasing dielectric constant alternating with regions of decreasing dielectric constant in at least one direction therein; (c) fabricating a plurality of dielectric sheets, each having a thickness and comprising a layer of host material and a 2D lattice of inclusions therein, said inclusions comprising a conducting material and having a characteristic spacing between their centers about or less $\frac{1}{10}$ of the wavelength, wherein the inclusions are arranged to form a 2D pattern of dielectric perturbations from the plurality of 2D patterns of dielectric perturbations; (d) arranging the plurality of dielectric sheets in a stacked layered arrangement to form a volume hologram comprising the 3D pattern of dielectric perturbations.

BRIEF DESCRIPTION OF THE DRAWINGS

Exemplary embodiments of the invention will now be described in conjunction with the drawings in which.

DETAILED DESCRIPTION OF THE PREFERRED EMBODIMENT

In a context of the present invention, a lattice of elements is said to be spatially modulated if one or more of lattice parameters are varied in space in a periodical or quasi-periodical manner. The lattice parameters that can be varied include lattice constant and size of the constituent elements.

To facilitate a better understanding of the invention, a short overview of basic features of volume holograms for changing a characteristic of an electromagnetic beam will now be given following an approach and notations of a monograph by Goodman, J. W., "Introduction to Fourier optics", McGraw-Hill, NewYork, 1996, which is incorporated herein by reference.

Figure 1:
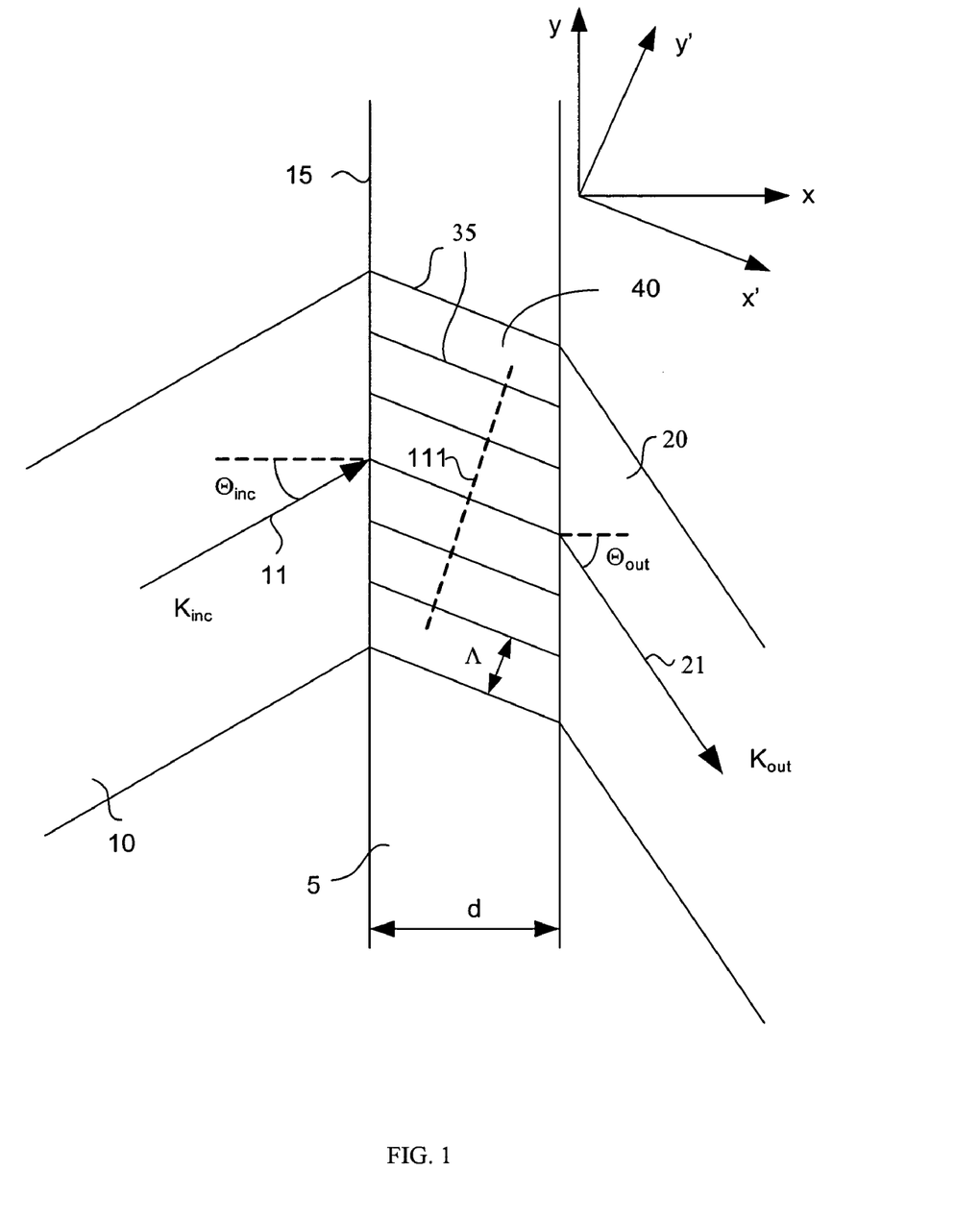
FIG. 1 is a diagram of a prior art volume hologram.

FIG. 1 schematically shows a side view of a volume hologram 5 for transforming an input electromagnetic beam 10 impinged upon a beam receiving surface 15 of the hologram into an output electromagnetic beam 20. The act of transforming is understood herein as an act of modifying one or several characteristics of the input beam so that a transmitted or reflected beam has the modified characteristics. A transmission type hologram is shown as an example. The electromagnetic beam is approximately monochromatic and has a spectral width $\Delta\lambda$ much smaller than a central wavelength $\lambda$ of the beam's spectrum. The hologram is formed by a slab of dielectric material transmissive for the input beam and incorporating a pre-determined grating-like 3D pattern of dielectric perturbations $\Delta\in(r)$ in a beam receiving region 40. The pre-determined 3D pattern of dielectric perturbations $\Delta\in(r)$, where a vector r denotes a location within the hologram, will also be referred herein as a dielectric pattern or a holographic pattern. The dielectric pattern can be designed to modify one or several characteristics of the input beam by diffraction upon the pattern, thereby transforming at least part of the input beam into the output beam having pre-determined characteristics. Beam characteristics that can be modified by a hologram commonly include a propagation direction of the beam and a beam shape understood herein as a spatial shape of a wavefront of the beam-forming radiation. In some cases, for example when the dielectric pattern is formed in a non-linear frequency-doubling material or by a running acoustic wave, frequency characteristics of the beam can also be modified.

In accordance with a holographic principle commonly employed in optics, the dielectric pattern required for producing a pre-determined output beam upon illumination of the hologram by an input beam can be obtained by imprinting an interference pattern of the two beams created in the beam receiving region of the dielectric slab into the dielectric constant of the slab. The two beams, which are in this context referred to as an object beam and a reference beam, are mutually coherent. Denoting an amplitude and a wavevector of the input or reference beam at a location r in the beam receiving region of the hologram as respectively $E_1(r)$ and $k_1(r)$ and an amplitude and a wavevector of the output or object beam as respectively $E_2(r)$ and $k_2(r)$, the dielectric pattern formed thereby can be described by a proportionality expression (1)

$$\Delta\in(r) \sim |E_1(r)|^2 + |E_2(r)|^2 + (E_1(r)^* E_2(r) \exp[i(r,\Delta k(r)) + i\Phi] + c.c.) \quad (1)$$

wherein a wavevector difference $\Delta k(r) = k_1(r) - k_2(r)$, (a,b) denotes a scalar multiplication of vectors a and b, $\phi$ is a constant wave shift between the two interfering waves, and "c.c." denotes a complex conjugate.

With reference to FIG. 1, in an illustrative example considered herein the input and output beams are plane waves, and the hologram 5 is designed to modify a propagation direction of the input beam, transforming the input beam incident on one side of the hologram with an incidence angle $\theta_{in}$ into the output beam 20 propagating away from the hologram in a direction 21 forming an output angle $\theta_{out}$ with a direction normal to an output surface of the hologram. In a Cartesian coordinate system (x',y',z') having y' axis directed in a direction of the wavevector difference $\Delta k$, which in this case is independent on the location, and axis z' directed normally to a plane of vectors $k_1, k_2$, the dielectric pattern can be described by a following relationship:

$$\in(r) = \in_0 + \in_1(r)\cos(Ky')$$

where $\in_0$ is an average dielectric constant of the hologram, $$K = |\Delta k| = \frac{2\pi}{\Lambda}$$

defines a spatial period $\Lambda$ of the dielectric pattern, and $\in_1(r)$ is an amplitude of the dielectric perturbations which can slowly vary in space within the beam-receiving region. The dielectric pattern has multiple regions of increasing dielectric constant alternating with regions of decreasing dielectric constant along a line 111 crossing the beam receiving region in the y' direction and can therefore be described as a volume grating with the grating period $\Lambda \geq \lambda/2$, which in the case of plane interfering waves described herein is a one-dimensional volume grating. If at least one of the input or output beams is not a plane wave, the dielectric pattern has a shape of a volume grating which ridges 35 are curved surfaces defined by equations $(r,\Delta k(r))=2\pi n$ with integer n. The pattern of dielectric perturbations will therefore also referred to herein as a holographic grating.

An important characteristic of a hologram is its efficiency $\eta$, which can be defined as a fraction of the input beam power transferred to the pre-defined output beam by the holographic grating. It is known in the art that relatively thick gratings having a grating thickness $d > \lambda$ and operating in a Bragg regime of diffraction are typically required to achieve high efficiency, for example above 50%. Such high-efficiency gratings are referred to herein us volume or three-dimensional (3D) gratings, and holograms incorporating such gratings are referred to herein as volume holograms as opposed to thin holograms having a theoretical diffraction limit of 36% which is a maximum of a first order Bessel function $J_1(\gamma)$.

When absorption of the input beam in the hologram material is small, the efficiency of the aforedescribed transmission type volume hologram formed by an interference of two plane waves can be estimated by using a relationship (3):

$$\eta = \frac{\sin^2(\Phi\sqrt{1+\chi^2/\Phi^2})}{1+\chi^2/\Phi^2} \quad (3)$$

In (3), $\chi$ and $\Phi$ are defined as $$\chi = \frac{\varsigma d}{2\cos\theta} \qquad (4)$$

$$\Phi = \frac{\pi n_1 d}{\lambda \cos\theta} \qquad (5)$$

where $\varsigma$ is a mismatch factor, described for example by Goodman, J. W., 1996, accounting for possible directional misalignment of the input beam with respect to the reference beam used to produce the grating, $\theta$ is an incidence angle of the input beam within the hologram satisfying Snell's law $$\sin(\theta)=\sin(\theta_{inc})/n, \; n=\sqrt{\in_0},$$

d is the hologram thickness, and $n_1$ is a representative of a modulation of a refractive index of the hologram corresponding to the modulation of the dielectric constant of the hologram:

$$n_1 = \frac{\varepsilon_1}{2\sqrt{\varepsilon_0}} \qquad (6)$$

A maximum efficiency for a given grating achieved when the mismatch factor $\varsigma=0$ can be computed from an equation (7)

$$\eta = \sin^2\Phi \qquad (7)$$

It follows from (7) that there is an optimum thickness $d_{opt}$ of the hologram for which the efficiency is maximized; this optimum thickness is defined by an equation $$d_{opt} = \lambda \frac{\cos(\theta)}{2n_1} \qquad (8)$$

The optical technology of the interference pattern imprinting in a photo-sensitive material such as photo-refractive glasses (PRG) typically produces relatively weak gratings characterized by the refractive index modulation $n^1 \sim 10^{-2 \sim 10^{-4}}$ corresponding to $d_{opt}/\lambda \sim 50 \ldots 5000$. A high-efficiency optical volume hologram can nevertheless be implemented in a physically relatively thin slab due to smallness of optical wavelength, typically on the order or less than a micron, corresponding to $d_{opt} \sim 0.05 \ldots 5$ mm.

No similar technology of direct interference pattern imprinting exists however for the microwave region of radiation corresponding to frequencies between ~10 GHz and ~1 THz, where alternative methods of holographic pattern fabrication are required. These alternative methods for creating a hologram for microwave radiation should preferably provide stronger gratings to realize high holographic efficiency in a physically thin structure, with $d_{opt}$ preferably not exceeding several centimeters.

The present invention is directed firstly towards providing an efficient volume hologram for modifying a microwave input beam, wherein the 3D holographic pattern of dielectric perturbations is formed in a multilayer artificial dielectric. Another aspect of the invention is directed towards a method of hologram fabrication enabling the fabrication of volume microwave holograms having high efficiency.

An exemplary embodiment of a volume hologram for modifying a characteristic of an input microwave beam having a central wavelength $\lambda$ is hereafter described with reference to FIG. 2 and FIG. 3 respectively depicting side and plane views of a section of the hologram.

The thick volume hologram 200, disposed to receive an input beam propagating in an input direction 201 through a beam receiving surface 204, is formed by M dielectric sheets 230 disposed in a sequential order one after another in a first direction 203 in a stacked layered arrangement. FIG. 2 depicts a side view of an illustrative embodiment of the hologram in which M=6; note that M>=10 is normally required to obtain a high efficiency hologram. Each dielectric sheet 230 has a plurality of inclusions 210 disposed on one side thereof, whereby a 2D lattice of the inclusions is formed on each of the dielectric sheets. A set of the M stacked 2D lattices of the inclusions formed on each of the dielectric sheets forms a 3D lattice wherein the inclusions are spaced apart from each other, and wherein a distance between adjacent inclusions is less than $\lambda'/3$, and preferably less than $\lambda'/10$, where $\lambda'$ is a central wavelength of the input beam in the hologram, $\lambda'=\lambda/n$. The set of M dielectric sheets 230 form a host dielectric material having a layered structure wherein the 3D lattice of inclusions 210 is incorporated.

The material, size, and a lattice density of the inclusions, i.e. a number of inclusions per unit volume, are selected to affect the dielectric properties of the host material at the wavelength of the input beam rather than to cause diffraction or scattering of the input beam on individual inclusions. The inclusions 210 are polarized in an electric field of the input electromagnetic beam 201 differently than the surrounding host dielectric material 205; when a large number of inclusions 210 is present on a scale of one wavelength $\lambda'$ of the input beam in the hologram 200, they provide an average polarization field having an effect on the input beam 201 approximately equivalent to changing the dielectric constant of the medium. The host dielectric material with a permittivity $\in_0$ and the 3D lattice of the inclusions incorporated therein form therefore an artificial dielectric having an effective dielectric constant $\in_r$ that can be expressed as a sum of the dielectric constant of the host material $\in_0$ and a contribution $\Delta\in'(r)$ from the 3D lattice of inclusions:

$$\in_r = \in_0 + \Delta\in'(r)$$

If the 3D lattice is regular and uniform, the contribution $\Delta\in'(r)$ of the 3D lattice of inclusions into the dielectric constant of the hologram at the wavelength $\lambda$ is approximately location-independent, provided that the size of the inclusions and the distance between centers of the adjacent inclusions is much smaller than $\lambda'$. However if the size of the inclusions, the spacing between their centers or their shape is spatially changing, $\Delta\in'(r)$ can vary depending on a spatial location r within the hologram. Therefore by spatially varying or modulating the shape, size or spacing of the inclusions 210 in the 3D lattice, a pre-determined holographic 3D pattern of dielectric perturbations required for modifying the input beam can be induced. This 3D pattern of dielectric perturbations can be computer-generated to approximate a holographic 3D pattern that would have been created by photo-imprinting a volume interference pattern of the reference and object beams, and therefore can be used for modifying characteristics of the input beam in a pre-determined way.

Although within the scope of present invention the 2D lattices and the 3D lattice can be irregular, regular lattices are preferred since it is advantageous to avoid random spatial variations of the lattice constant, the size and the shape of the inclusion which can cause unwanted scattering of the input beam thereby detrimentally affecting the efficiency of the hologram 200.

Different embodiments of the hologram can be envisioned wherein the inclusions can have different shape and be either non-conducting with a dielectric constant different from the dielectric constant of the host material, or conducting, for example fabricated from a metal or a semiconductor. The inclusion can also be in the form of voids in the host material.

Figure 2:
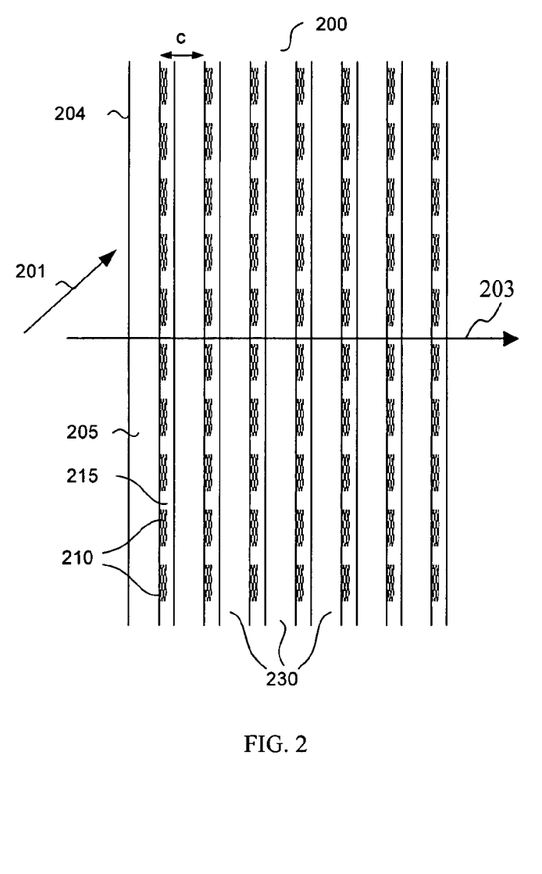
FIG. 2 is a side view of a volume multilayer artificial dielectric hologram in accordance with an embodiment of the invention.
Figure 3:
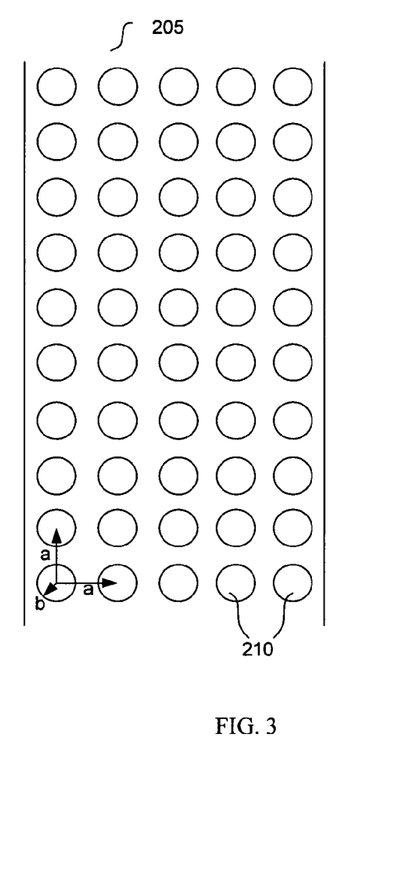
FIG. 3 is a front view of the volume multilayer artificial dielectric hologram shown in FIG. 2.

In an exemplary embodiment of the volume hologram schematically shown in FIG. 2 and FIG. 3, the inclusions are conducting disks of radius "b" disposed on sheets of dielectric material 205 in a regular cubic 2D lattice with a lattice constant "a". A non-exclusive list of possible dielectric materials 205 can for example include polymers, ceramics or composite materials such as such as Rogers 3003 material commercially produced by Rogers Corporation commonly used for microwave circuit boards. The dielectric sheets with the conducting discs are laminated with a bonding material 215 having a permittivity close to the permittivity of the dielectric sheets, and bonded to each other to form a layered structure, with a distance "c" between the 2D lattices of the metallic disks on adjacent dielectric sheets less than $\lambda'/3$ and preferably about or less than $\lambda'/10$. The 2D lattice parameters "a" and "b" satisfy a condition $2b < a < \lambda'/10$.

The effective permittivity of the artificial dielectric composed of the disk inclusions can be calculated from relations provided by Brown, J., and Jackson, W. in a paper entitled "The relative permittivity of tetragonal arrays of perfectly conducting thin discs", published in Proc. IEE, paper 1702R, Jan. 1955:

$$\varepsilon_r = \varepsilon_0 + \frac{\varepsilon_0 a/c}{\left(1.5\left(\frac{a}{b}\right)^3 - 0.36\right)} \quad \text{for } c/a \geq 0.6 \quad (12)$$

$$\varepsilon_r = \varepsilon_0 + \frac{aN}{1 - \frac{1}{2}\left(\frac{aN}{\varepsilon_0}\right)} \quad \text{for } c/a \leq 0.6 \quad (13)$$

where N is a number of disks per unit area, and $\alpha$ is defined as $$\alpha = \frac{\pi \varepsilon_0 b^2}{2}\left[\left(1 - \frac{0.441c}{b}\right)^2 + \frac{0.058c^3}{b^3}\left(1 + \frac{0.441c}{b}\right)\right]. \quad (14)$$

Figure 4:
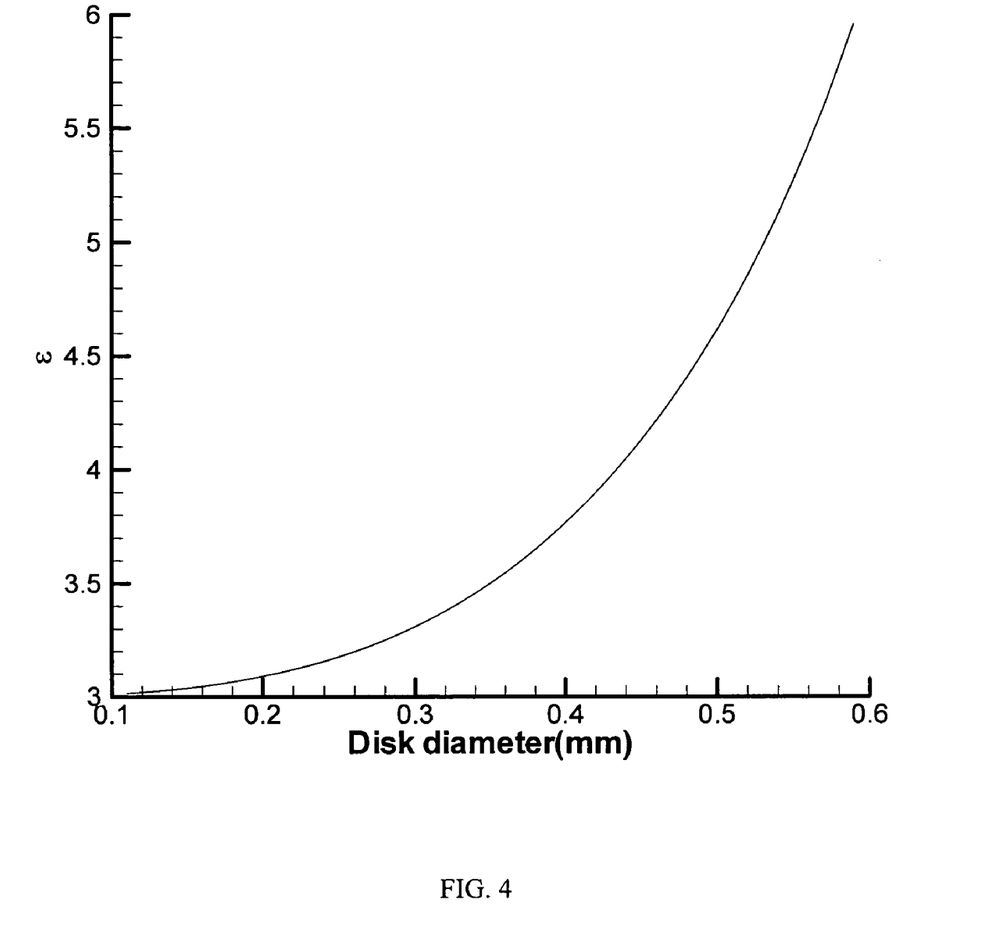
FIG. 4 is a plot of dielectric constant of an artificial dielectric.

A dependence of the effective permittivity of the multi-layered volume hologram of the aforedescribed type having c=0.5 mm, a=0.6 mm and $\in_0$=3 on the disk diameter 2*b is depicted in FIG. 4. This set of disk and lattice parameters is appropriate for providing an artificial dielectric for application in a wavelength range of $\lambda \geq 1$ cm, corresponding to frequencies about 30 GHz or less. It is evident from FIG. 4 that a wide range of permittivity values can be realized in this artificial dielectric by changing the disk diameter. In particular, by spatially modulating the diameter of disk inclusions in a multi-layer slab of the artificial dielectric, a volume diffraction grating with the refractive index modulation parameter $n_1$~0.1 or larger can be fabricated, enabling the realization of a high-efficiency multi-layer volume hologram for operation in the microwave frequency range with an optimal thickness $d_{opt}$ defined by expression (8) of a few centimeters or less.

Note that the microwave hologram of the present inventions can be fabricated to modify not only the input direction, but also other characteristics of the input beam such as the shape of the input beam. For example, embodiments wherein the 3D dielectric pattern is designed to simultaneously re-direct and collimate a diverging microwave beam can be realized.

Figure 5:
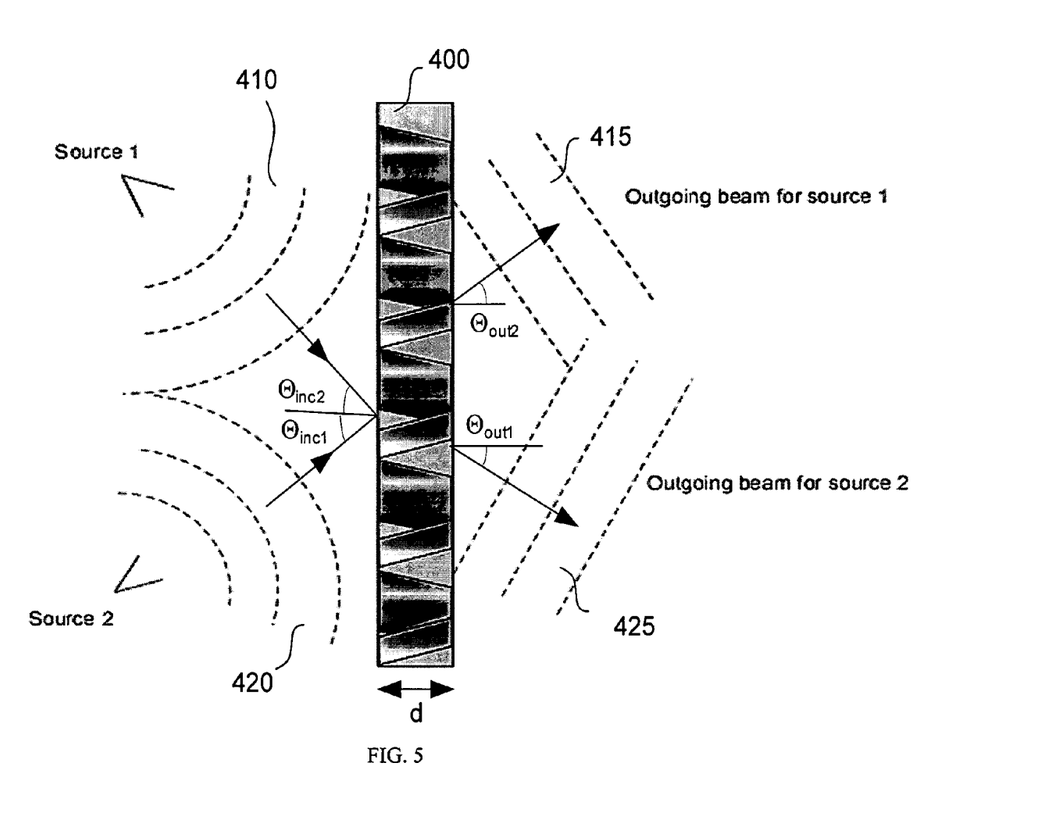
FIG. 5 is a diagram of a multiplexed volume hologram.

In other embodiments, a multiplexed dielectric pattern can be realized for simultaneously modifying characteristics of two or more input microwave beams. FIG. 5 shows an application of such a hologram, wherein two diverging microwave beams 410 and 420 impinge on the same surface area of a volume microwave hologram 400 incorporating a multiplexed 3D volume grating pattern induced in the beam receiving region by an appropriate modulation of the 3D lattice of inclusions. The hologram simultaneously transforms the input beams 410 into a collimated beam 415 having a direction different from the input direction of the beam 410, and transforms the input beams 420 into a collimated beam 425 having a direction different from the input direction of the beam 420. The multiplexed 3D grating pattern can be designed by computer simulations from a multiplexed interference pattern of the four beams, and consequently adjusting the pattern to minimize cross-coupling between the input/output beam pears.

In other embodiments, the volume microwave hologram can be used for beam splitting and beam combining applications, wherein the 3D pattern is designed from multiplexed interference patterns of a single input beam and multiple output beams, or vice versa multiple input beams and a single output beam. Generally, embodiments wherein the volume microwave hologram of the present invention wherein N input beams are directed into M output ports can be envisioned wherein the 3D holographic patterns are produced by multiplexing multiple interference patterns.

In other embodiments, the present invention can be used for providing volume holograms for modifying characteristics of an input electromagnetic beam having a wavelength outside of the microwave range. An optic multi-layer volume hologram incorporating a holographic pattern induced by appropriate modulation of a 3D lattice of inclusions in accordance with present invention can be envisioned. Such a hologram can be realized, for example, using dielectric or semiconductor materials and modern high-resolution lithographic technologies.

In another aspect of the invention, a method of fabrication of a multilayer volume microwave hologram for modifying a microwave beam is provided. The method includes the steps of:

1) Identifying target characteristics of the input and output microwave beams. These target characteristics include a center wavelength, the input and output directions of the microwave beam, an input wave-front shape and an output wave-front shape of the microwave beam.

2) Computing an interference pattern of the input and output microwave beams and using it to determine a 3D pattern of dielectric perturbations $\Delta\delta(r)$ for transforming the input microwave beam into the output microwave beam.

3) Fabricating a set of M dielectric sheets, each sheet having a 2D lattice of closely spaced inclusions imbedded within or upon it, said inclusions in each sheet arranged to induce the 3D pattern of dielectric perturbations $\Delta\in(r)$ when the dielectric sheets are assembled together in a stacked layered arrangement having a pre-determined spacing between the adjacent 2D lattices of inclusions.

4) Bonding the set of M dielectric sheets together one after another in the stacked layered arrangement to form a volume multi-layer hologram comprising the 3D pattern of dielectric perturbations.

In the aforedescribed exemplary embodiment shown in FIG. 2, 3 wherein the inclusions are conducting disks supported by dielectric sheets, relationships (12)–(13) can be used to compute a 3D pattern of spatial variations of the disk diameter consisting of M 2D patterns of spatial variation of the disk diameter required to produce the 3D pattern of dielectric perturbations for modifying the input microwave beam. The 3D pattern of the dielectric perturbations can be computer-generated using computer simulations of the interference pattern of the reference and object beams. The process of computing the set of M 2D patterns of spatial variations of the disk diameter can include, for example, the steps of a) computing an interference pattern of the reference and object beams, b) determining a starting 3D pattern of dielectric perturbations $\Delta \in_{ijk}$ approximating the computed interference pattern, wherein indexes i and j determine location of a disk inclusion in k-th dielectric sheet when the dielectric sheets are assembled in a multi-layer hologram, for a selected lattice period "a" of the disk inclusions and a selected sheet thickness "c", wherein both "a" and "c" are less than $\sim\lambda/10$, c) computing a 3D matrix b with elements $b_{ijk}$ specifying disk diameters for all disk inclusions of the 3D lattice of inclusions required for inducing the starting 3D pattern of dielectric perturbations in a multi-layer structure formed by the assembled stack of M dielectric sheets, d) performing computer simulations of diffraction of the input beam in the multi-layer hologram, e) if required, optimizing the holographic pattern for example to increase the hologram efficiency by iteratively adjusting spatial modulation of the disk diameter described by the matrix $b_{ijk}$ and repeating step d).

Diffraction of the input beam in the multi-layer hologram can be computed using a relatively simple method suggested by Alferness, R.in "Analysis of optical propagation in thick holographic gratings", Applied Physics, Vol. 7, 1975, pp. 29–33, which employs a known transfer matrix representation of a hologram. Following this method, each dielectric sheet incorporating a 2D lattice of inclusions can be considered as a thin, essentially 2D, grating operating in a Raman-Nath regime of diffraction, which transfer matrix can be computed using well-known straightforward methods. A transfer matrix of the volume multi-layer hologram is then computed from the M transfer matrixes of the thin holograms by matrix multiplication.

The aforedescribed method of present invention was verified by fabricating two microwave volume holograms for modifying characteristics of microwave beams at 30 GHz frequency, corresponding to $\lambda=1$ cm in the air.

First, a volume hologram with a single interference pattern designed to couple an input plane wave having $\theta_{inc}=+55°$ into a first order transmit mode having $\theta_{out}=+55°$, with a sign convention as shown in FIG. 1.

The hologram was made by laminating 81 layers of Rogers 3003 material of 0.020" thickness with $\in_0=3.0$. Arlon CLTE-P bonding material with $\in=2.94$ was used to laminate the layers. Careful consideration was given to the selection of the bonding material, which was chosen to minimise a dielectric constant difference between the host Rogers 3003 material and the bonding film. A metallized side of each layer of the Rogers 3003 material was patterned and etched to form a pre-determined 2D lattice of conducting disks. The volume holographic pattern of dielectric perturbation was designed with the average dielectric constant $\in=3.6$ and $\in_1=0.4$. The number of layers was chosen so that the hologram thickness would be close to an optimum value which was calculated using expression (8) to be ~4.2 cm.

The hologram was measured with a setup composed of two similar microwave lenses fed by two horn antennas connected respectively to a microwave source and a microwave receiver. By setting the lenses at the proper distance from each other, their beam waists coincided with the mid-point of the line that connects the lenses, where the hologram was placed. FIG. 5 shows a plot of the measured diffraction efficiency versus angular orientation of the receive antenna. It can be seen that about 70% of the power has been coupled with high angular selectivity into the transmit output beam propagating away from the hologram along $\theta_{out}=52°$. The measured efficiency, although lower than 100%, was considerably higher than the maximum achievable efficiency of 36% for a thin hologram.

Figure 6:
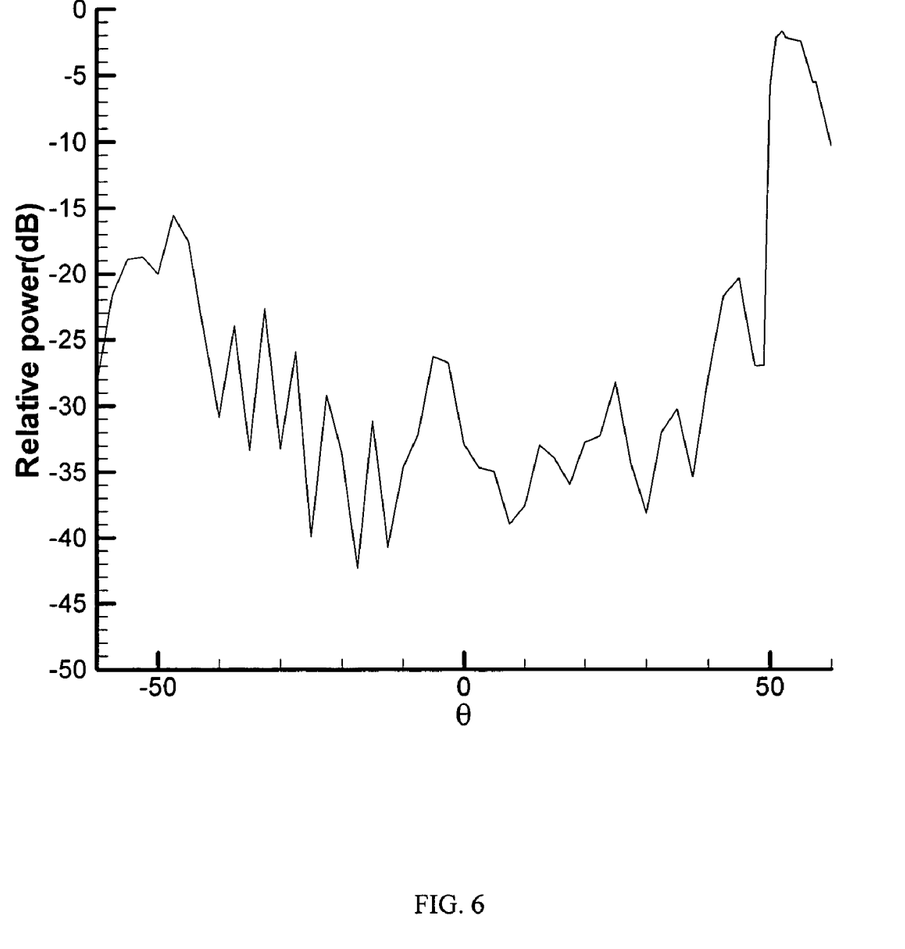
FIG. 6 is an experimental plot of hologram efficiency.
Figure 7:
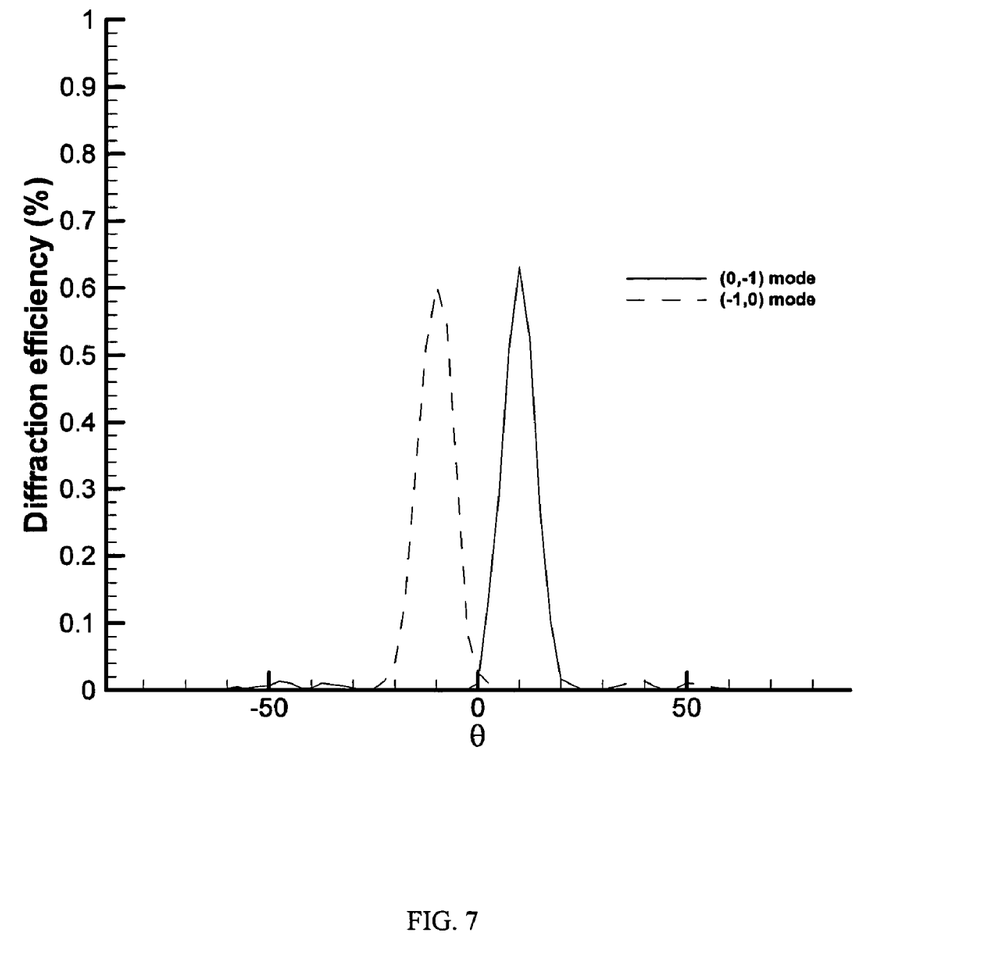
FIG. 7 is an experimental plot of a multiplexed hologram efficiency.

Second, a multiplexed volume hologram was fabricated wherein the 3D pattern of dielectric perturbations was designed to change directions of two input beams as shown in FIG. 4. A method described by Alferness, R., Case, S. K.in "Coupling in doubly exposed holographic grating", j. Opt. Soc. Am., Vol. 65(6), 1975, pp. 730–739 was used to design the multiplexed volume grating for the hologram. A computer code was developed to determine design parameters such as $\in_0$, $\in_1$, and d to achieve high coupling between the reference and object beam pairs 410, 415 and 420, 425 and a low cross coupling between the two pairs. The multiplexed hologram was designed to operate at 30 GHz. The volume grating pattern was generated from two superimposed incoherent interference patterns corresponding to two object and reference beams at $\theta inc1,2=\pm45°$ to $\theta out1,2=\pm10°$. Index modulation was set at 0.12 for both interference patterns. The structure was composed of 86 layers of 3003 Rogers material of $\in_0=3.0$ and 0.15" thickness bonded together by CLTE-P prepreg material of $\in_0=2.94$ and 0.0024" thickness. Two prepreg sheets were used per interface to keep the thickness of each layer at a design value of 0.020". FIG. 6 shows measured angular distribution of the output beams demonstrating high efficiency and low cross-coupling between the beams. The labels "(0,–1) mode" and "(–1,0) mode" refer to output beams excited respectively by an input beam having $\theta inc =-45°$ and $\theta inc =+45°$.

The apparatus and method of present invention can be utilized to translate many optical applications of volume holograms into the microwave band, including separation of two beams having the same frequency and polarization but different angles of arrival that proved to be a difficult problem in the microwave band, for beam combining which translates into power combining in the microwave band, or for data processing in the microwave band similar to holographic data processing in optics.

Of course numerous other embodiments may be envisioned without departing from the spirit and scope of the invention.

What is claimed is:

1. A volume hologram for modifying a characteristic of an input electromagnetic beam propagating in an input direction, said volume hologram comprising:

a host material having a dielectric constant and a beam receiving region for receiving the input electromagnetic beam having a center wavelength $\lambda$ when propagating in the volume hologram;

a 3D lattice of inclusions spaced from one another incorporated in the beam receiving region of the host material, each said inclusion having a size and a center, wherein said inclusions are disposed with a spacing between centers of adjacent inclusions smaller than one third of the center wavelength for providing the volume hologram with an effective dielectric constant $\in_r$ different from the dielectric constant of the host material, and wherein said inclusions are arranged for inducing a pre-determined 3D pattern of dielectric perturbations in the beam receiving region of the host material, said pre-determined 3D pattern of dielectric perturbations having multiple regions of increasing dielectric constant alternating with regions of decreasing dielectric constant along a straight line crossing the beam receiving region, for modifying the input electromagnetic beam by diffraction thereupon.

2. A volume hologram as defined in clam 1, wherein the host material comprises a plurality of M dielectric sheets disposed sequentially in a first direction and forming a stacked layered structure crossing the input direction, and wherein each of the M dielectric sheets incorporates a 2D modulated lattice of the inclusions with a lattice period about or less than $0.1\lambda$ wherein the inclusions are arranged for inducing a 2D pattern of dielectric perturbations, said 2D pattern of dielectric perturbations having multiple regions of increasing dielectric constant alternating with regions of decreasing dielectric constant in at least one direction therein, and wherein a plurality of M 2D patterns of dielectric perturbations thereby provided form the pre-determined 3D pattern of dielectric perturbations.

3. A volume hologram as defined in claim 2 comprising at least 10 dielectric sheets.

4. A volume hologram as defined in clam 1, wherein the host material and the 3D lattice of inclusions form an artificial dielectric.

5. A volume hologram as defined in clam 2, wherein the inclusions comprise a dielectric having a dielectric constant different from the dielectric constant of the host material.

6. A volume hologram as defined in clam 2, wherein the inclusions comprise voids.

7. A volume hologram as defined in clam 2, wherein the inclusions comprise a conducting material.

8. A volume hologram as defined in clam 7, wherein the conducting material is one of a metal, a semi-metal and a semiconductor.

9. A volume hologram as defined in clam 2, wherein the inclusions have a shape of a disk.

10. A volume hologram as defined in claim 2, wherein the inclusions are conducting disks disposed within or upon the dielectric sheets.

11. A volume hologram as defined in claim 1, wherein the pre-determined 3D pattern of dielectric perturbations is induced by spatial variations of the characteristic spacing between the inclusions in the host material.

12. A volume hologram as defined in claim 1, wherein the pre-determined 3D pattern of dielectric perturbations is induced by spatial variations of the characteristic size of the inclusions.

13. A volume hologram as defined in claim 2, wherein at least one of the plurality of 2D patterns of dielectric perturbations is induced by spatial variations of at least one of the size of the inclusions and the lattice period.

14. A volume hologram as defined in claim 2, wherein at least one of the 2D patterns of dielectric perturbations comprise a periodic spatial modulation of the dielectric constant of the volume hologram.

15. A volume hologram as defined in claim 1, wherein the 3D pattern of dielectric perturbations is for directing N input electromagnetic beams into M output ports disposed at locations proximate to the host material.

16. A volume hologram as defined in claim 1 wherein the 3D pattern of dielectric perturbations is for modifying a microwave beam having a frequency between 10 GHz and 1000 GHz.

17. A volume hologram as defined in claim 1 wherein the electromagnetic beam has a wave front and wherein said modifying of the electromagnetic beam includes modifying spatial shape of the wave front of the electromagnetic beam.

18. A method of fabrication of a volume microwave hologram for modifying a microwave beam, said method comprising steps of identifying parameters of input and output microwave beams, said parameters including a wavelength, an input direction and an output direction of the microwave beam, an input wave front shape and an output wave front shape of the microwave beam;

identifying a plurality of 2D patterns of dielectric perturbations and a spatial separation between said 2D patterns for forming a 3D pattern of dielectric perturbations from the plurality of stacked 2D patterns of dielectric perturbations for changing at least the direction of the microwave beam from the input direction to the output direction by diffraction on the 3D pattern of dielectric perturbations, said 2D patterns of dielectric perturbations including multiple regions of increasing dielectric constant alternating with regions of decreasing dielectric constant in at least one direction therein;

fabricating a plurality of dielectric sheets, each having a thickness and comprising a layer of host material and a 2D lattice of inclusions incorporated therein, said inclusions comprising a conducting material and having a characteristic spacing between their centers about or less $\frac{1}{10}$ of the wavelength, wherein the inclusions are arranged to form a 2D pattern of dielectric perturbations from the plurality of 2D patterns of dielectric perturbations;

arranging the plurality of dielectric sheets in a stacked layered arrangement to form a volume hologram comprising the 3D pattern of dielectric perturbations.

19. A volume hologram for modifying an input microwave beam, said volume hologram comprising:

a plurality of dielectric sheets disposed sequentially one after another in a first direction to form a stack of layers for receiving the microwave beam propagating in an input direction at an acute angle with the first direction at a first location and for outputting an output microwave beam in an output direction from a second location, said microwave beam having a wavelength $\lambda$ corresponding to a frequency between 10 and 1000 GHz, each of the dielectric sheets comprising:

a) a sheet of dielectric material, b) a 2D lattice of conducting elements disposed over the sheet of dielectric material spaced from one another, said conducting elements having a characteristic size and a characteristic spacing between their centers about or less than one tenth of the wavelength, c) a laminating layer disposed over the 2D lattice of conducting elements, wherein the 2D lattices of conducting elements in the stack of layers are spaced less than one third of the wavelength apart, and wherein at least one of the characteristic size of the conducting elements and the characteristic spacing therebetween in at least some of the dielectric sheets are modulated in a direction normal to the first direction for inducing a pre-determined 3D pattern of dielectric perturbations for modifying the input electromagnetic beam by means of diffraction thereupon.

* * * * *